(12) United States Patent
Jequier

(10) Patent No.: US 8,633,202 B2
(45) Date of Patent: Jan. 21, 2014

(54) CRYSTALLINE LEVOFOLINIC ACID AND PROCESS FOR ITS PREPARATION

(75) Inventor: Pascal Jequier, Neuchatel (CH)

(73) Assignee: GMT Fine Chemicals SA, Couvet (CH)

( * ) Notice: Subject to any disclaimer, the term of this patent is extended or adjusted under 35 U.S.C. 154(b) by 9 days.

(21) Appl. No.: 13/426,021

(22) Filed: Mar. 21, 2012

(65) Prior Publication Data
US 2012/0245177 A1    Sep. 27, 2012

(30) Foreign Application Priority Data

Mar. 21, 2011  (EP) .................................. 11158959

(51) Int. Cl.
*C07D 475/04* (2006.01)
*A61K 31/519* (2006.01)
*A61P 35/00* (2006.01)

(52) U.S. Cl.
USPC ....................................... 514/262.1; 544/258

(58) Field of Classification Search
USPC ........................................ 544/258; 514/262.1
See application file for complete search history.

(56) References Cited

U.S. PATENT DOCUMENTS

| 5,134,235 A | 7/1992 | Mueller et al. |
| 2008/0153849 A1 | 6/2008 | Giancarlo et al. |

FOREIGN PATENT DOCUMENTS

WO    2008144953 A1    12/2008

OTHER PUBLICATIONS

European Search Report for Corresponding European Application No. 11158959.4 dated Sep. 30, 2011.

*Primary Examiner* — Bruck Kifle
(74) *Attorney, Agent, or Firm* — McCormick, Paulding & Huber LLP

(57) ABSTRACT

The present invention relates to stable crystalline (6S)—N (5)-formyl-5,6,7,8-tetrahydrofolic acid, commonly referred to as levofolinic acid, in essentially pure 6S diastereomeric form, and to a process for its preparation.

16 Claims, 2 Drawing Sheets

CRYSTALLINE LEVOFOLINIC ACID AND PROCESS FOR ITS PREPARATION

CROSS REFERENCE TO RELATED APPLICATION

This application is entitled to the benefit of and incorporates by reference essential subject matter disclosed in European Patent Application No. 11158959.4 filed on Mar. 21, 2011.

FIELD OF THE INVENTION

The present invention relates to the compound (6S)—N(5)-formyl-5,6,7,8-tetrahydrofolic acid in stable crystalline form and to a process for its production.

BACKGROUND OF THE INVENTION

Folinic acid is used in cancer chemotherapy, to counteract the side-effects of treatments involving the drug methotrexate, or in synergistic combination with the chemotherapy agent 5-fluorouracil. Folinic acid is generally administered in the form of its calcium or sodium salts.

Folinic acid exists in diastereoisomeric forms, depending on the R or S configuration at the carbon atoms identified as chiral in the structural formula below:

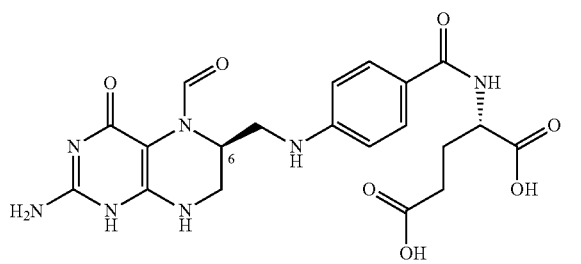 [SMILES: Nc1nc(=O)c2c([nH]1)NC[C@H](CNc1ccc(C(=O)N[C@@H](CCC(=O)O)C(=O)O)cc1)N2C=O]

The chiral carbon atom in the glutamic acid moiety retains the structure of the natural aminoacid. The other chiral center is the carbon atom identified as 6 in the formula above; as it happens with most biological enantiomeric molecules, only the form with configuration S at this carbon, that is, the compound (6S)—N(5)-formyl-5,6,7,8-tetrahydrofolic acid, is biologically active. This form of the acid is commonly referred to in the field as levofolinic acid, and its salts as levofolinates, terms that will be adopted in the description that follows and in the claims.

Diastereomerically enriched or pure forms of levofolinic acid are generally produced, directly in form of pharmaceutically acceptable salts, through crystallization.

An example of such processes is given in U.S. Pat. No. 5,134,235, disclosing the production of alkaline-earth salts of levofolinic acid in enriched form compared to the racemic mixture.

Patent application US 2008/0153849 A1 discloses a method by which it is possible to prepare either the racemic mixture of dextrofolinic and levofolinic acid in crystalline form, or pure levofolinic acid in amorphous form.

At present, it is not known yet a method affording the preparation of essentially pure levofolinic acid in crystalline form; the production of this compound, in a diastereoisomerically pure form, is desirable, as it would provide a convenient way of producing pharmaceutical salts of the acid in 6S pure form and could also be directly used for new pharmaceutical formulation without needing the previous preparation of a salt.

It is thus object of the present invention to provide the compound (6S)—N(5)-formyl-5,6,7,8-tetrahydrofolic acid in diastereoisomerically pure and stable crystalline form, as well as a process for its preparation.

SUMMARY OF THE INVENTION

These objects are achieved by the present invention which, in an aspect thereof, provides a process for the preparation of crystalline folinic acid in essentially pure 6S-form, comprising the steps of:

preparing a first aqueous or hydroalcoholic solution, having a pH value higher than 4.5, of a soluble levofolinate salt;

providing a batch of water, or of a hydroalcoholic mixture containing up to 60% v/v of alcohol, pre-heated at a temperature between 30 and 60° C.;

forming a second solution, by adding said first solution and a second acid to said batch of water or hydroalcoholic mixture, operating in such a way that the levofolinate salt concentration in the second solution never exceeds 4% w/v, the pH value of the second solution always remains in the range between 3.0 and 4.5, and the temperature of the second solution always remains in the range between 30 and 60° C.;

upon completion of the addition of said first solution to said batch of water or hydroalcoholic mixture, stirring the thus formed second solution while the precipitation of levofolinic acid occurs, maintaining the solution at a temperature between 30 and 60° C., monitoring the pH and continuously adding said second acid to keep the pH stable, until it is observed that the pH value becomes stable with no need of further addition of said second acid, indicating the end of the crystallisation of levofolinic acid;

recovering the crystalline levofolinic acid thus formed.

DETAILED DESCRIPTION OF THE INVENTION

Figure 1:
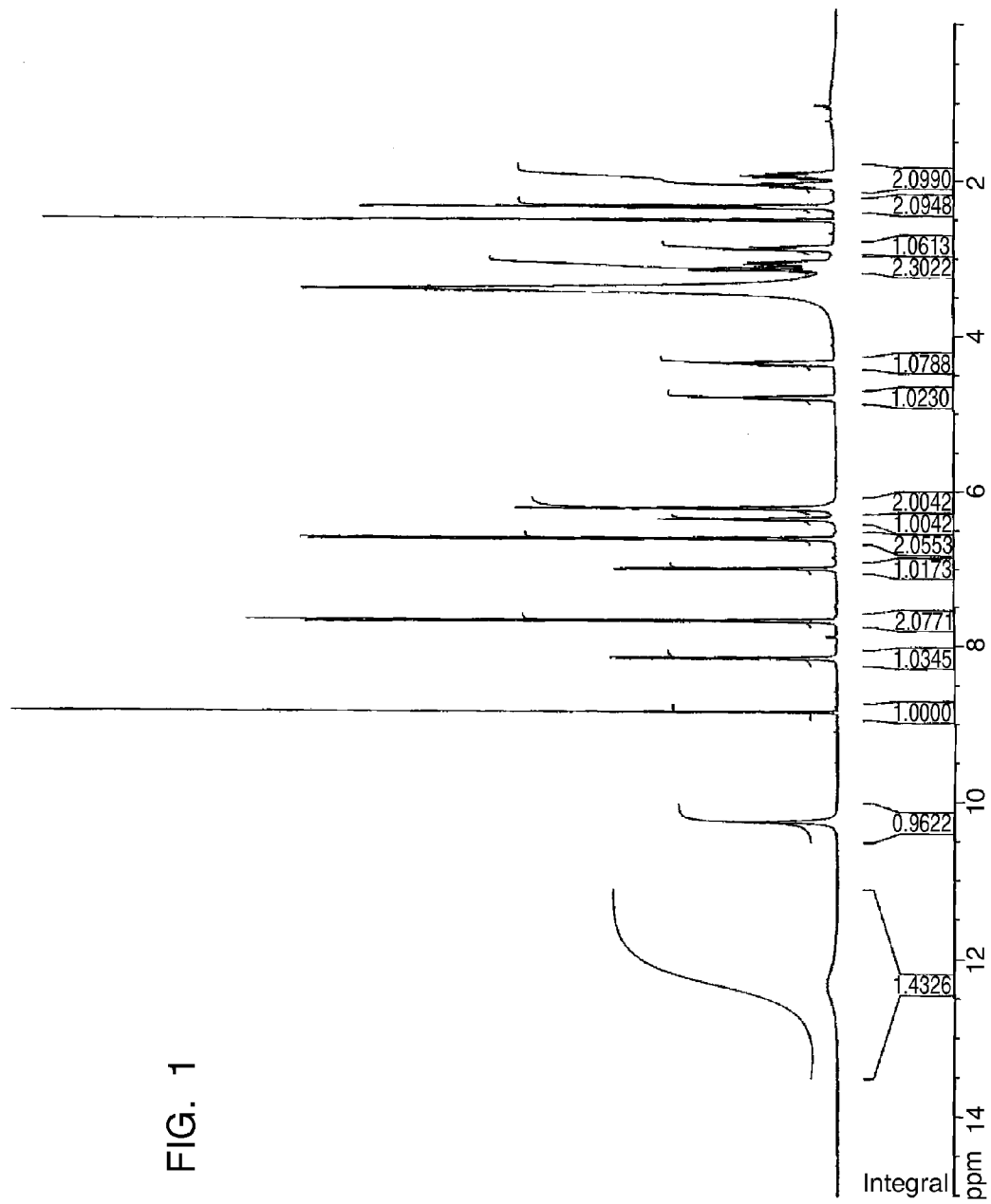
FIG. 1 shows the NMR spectrum of levofolinic acid prepared according to the invention.

By the term "essentially pure", as used in the present text and in the appended claims, it is meant levofolinic acid having diastereoisomerical purity of at least 98%. Concentration values reported as w/v percentages indicate the grams of solute per 100 cc of solution.

The first step of the process of the invention consists in preparing a first aqueous or hydroalcoholic solution of a soluble levofolinate salt, and controlling its pH value at a value higher than 4.5. In case of use of a hydroalcoholic solution, the preferred alcohols are methyl alcohol, ethyl alcohol, isopropyl alcohol and their mixtures.

The first solution may be obtained by directly solubilizing in water or in a water-alcohol mixture a soluble salt of the acid. The most soluble salts are the alkaline-metal salts, and preferably the sodium salt; an alkaline metal salt of levofolinic acid may be dissolved in water at room temperature up to a concentration of about 30% w/v. The first solution may also be prepared starting from an alkaline-earth metal salt, typically the calcium salt; as these salts have reduced solubility in water or hydroalcoholic mixtures, in this case it is preferable to work at relatively high temperatures, up to about 80° C. under protective atmosphere (e.g., nitrogen). Finally, it is possible to form an aqueous or hydroalcoholic suspension of an alkaline-earth metal salt, at a temperature at which the salt is scarcely soluble (e.g., room temperature); the salt is then solubilized by exchange of the cation, e.g. by addition of sodium carbonate; in these conditions, the carbonate of the alkaline-earth metal is formed, that precipitates and is separated e.g. by centrifugation and/or fine filtration; the result is a sodium levofolinate solution.

Apart, a batch of water or of a hydroalcoholic mixture, pre-heated at a temperature of at least 30° C. and not higher than 60° C., is made ready; preferably, the batch temperature is about 45° C. In case of use of the hydroalcoholic mixture, this can contain up to 60% v/v of alcohol, depending on the alcohol (or alcohols) preferably, the alcohol content is 5-10%. Again, methyl alcohol, ethyl alcohol, isopropyl alcohol or their mixtures are preferred for preparation of the hydroalcoholic mixture.

The first solution is then slowly added to the batch of water or of hydroalcoholic mixture, thus forming a second solution. In this step levofolinic acid crystallizes out of the formed solution. The second solution is thus constituted by the mother liquor from which the product is crystallized. The dynamic characteristics of this mother liquor are of interest for the control of the process. The addition of the first solution to said batch must be done in such a way that the levofolinic acid concentration in the second solution never exceeds the concentration of 4% w/v and remains ideally between 1 and 2.5% w/v while levofolinic acid crystallizes out of the solution. This operation takes place under pH control of the second solution, that must be kept constantly in the range between 3.0 and 4.5. During this phase, levofolinate anions recombine with $H^+$ ions present in the second solution, forming crystalline levofolinic acid, which is scarcely soluble in water or in hydroalcoholic mixtures in the proposed pH range.

Recombination with $H^+$ ions gives rise to an increase of pH that must be compensated by addition of a suitable second acid, e.g., diluted hydrochloric acid, in order to maintain the pH in the indicated range. Another way to control this step of the process is to observe the second solution during the addition of the first solution. In fact, if the concentration of levofolinic acid exceeds the upper limit of 4% w/v, due to a too fast addition of the first solution, the second solution becomes cloudy and the amorphous form of levofolinic acid precipitates.

Operating in such a way that the second solution always remains crystal clear assures that the condition of remaining below said limit of 4% is met.

This step may be carried out adding both the first solution and the second acid needed to keep the pH value in the indicated range to the water or hydroalcoholic batch slowly and continuously, or in small subsequent amounts. Acids that can be used are the non-oxidising acids, and acids that do not react with levofolinic acid or its salts; preferred are the mineral acids such as $H_2SO_4$, $H_3PO_4$ and, particularly preferred, HCl.

In case of addition of the first solution in small amounts to the batch of water or hydroalcoholic mixture, after each addition, the pH increase stops when the levofolinate anion has been essentially completely converted into the crystalline acid, and the next addition of an amount of first solution may take place.

This step must also be carried out and under control of temperature, that must be brought or maintained in the range 30-60° C.

Control of levofolinate concentration, pH and T are necessary because levofolinic acid is an unstable compound, as discussed e.g. in U.S. Pat. No. 6,441,168 B1, and is easily converted into by-products if the pH becomes lower than 3.0, or if during pH lowering the temperature reaches 60° C. or even higher values.

When the first solution has been completely added to the water or hydroalcoholic batch, either continuously or in small subsequent amounts, the second solution thus obtained is maintained under stirring at the temperature in the range of 30-60° C., while monitoring the pH trend and controlling it by addition of the second acid; when the pH value becomes stable with no need of further addition of the second acid, the formation of crystalline levofolinic acid is complete.

Finally, the crystalline solid may be recovered with known means, such as centrifugation and/or filtration, followed by drying of the product e.g. by removal of solvent traces under reduced pressure.

The compound (6S)—N(5)-formyl-5,6,7,8-tetrahydrofolic acid in stable crystalline form is a further aspect of the invention. This compound in stable crystalline form has not been reported in the prior art. The crystalline form of the compound is characterized by peaks at the following 2θ angle values in the XRD diagram (2θ values are given with an approximation of ±0.2°):

14.4
17.3
17.7
18.3
19.7
20.0
22.1
23.3
27.3

The invention will be further illustrated by the following examples.

EXAMPLE 1

Production of Crystalline Levofolinic Acid 100 kg of calcium levofolinate pentahydrate (166 mol) are suspended in 500 litres (L) of purified water. The suspension is heated at 40° C. and is then decalcificated by addition of 25 kg of sodium carbonate (236 mol); acetic acid is added to maintain the pH of the system at a value of about 8.0. The formed calcium carbonate is eliminated by centrifugation and the obtained sodium levofolinate solution is clarified by fine filtration. The filtered solution is diluted with water to a volume of 850 L and 51 L of isopropanol are added thereto, thus forming a first solution. The first solution is then progressively added, during 1 hour under stirring, to a hydroalcoholic batch formed by 350 L of water and 35 L of isopropanol previously heated at 45° C. During this addition, the pH is monitored and kept in the range between 3.5 and 4.0 by progressive addition of 50 L of a 25% b.w. solution of HCl; the temperature is in its turn slowly decreased to 35° C. At the end of the addition phase (i.e., the operation of adding the first solution to the hydroalcoholic batch), the obtained solution is kept at 35° C. under stirring, while controlling the pH with further additions of the same HCl solution used before, until a stable value of 4.0 is reached; a total of 50 liters of HCl solution is added in the two phases. Levofolinic acid crystallizes out of the obtained solution during the addition phase and the subsequent stirring period. The crystallized levofolinic acid is then isolated by centrifugation, washed with water and dried under reduced pressure. 80 kg of product are obtained.

A first specimen of the thus obtained product is submitted to a $^1$H-D$_2$O NMR analysis at 400 MHz; a second specimen of the product batch is submitted to XRD analysis. The resulting spectra are reported in FIG. 1 and in FIG. 2, respectively, and the identification of signals in the NMR spectrum are reported in Table 1 below.

TABLE 1

| Chemical shift (ppm) | Number of protons | Multiplicity | Attribution |
|---|---|---|---|
| 1.8-2.1 | 2 | multiplet | —CH—CH$_2$—CH$_2$—COOH |
| 2.3 | 2 | triplet | —CH—CH$_2$—CH$_2$—COOH |
| 2.8-3.4 | 4 | multiplet | —CH$_2$—CH*—CH$_2$— |
| 4.3 | 1 | multiplet | —CH—CH$_2$—CH$_2$—COOH |
| 4.8 | 1 | multiplet | —CH$_2$—CH*—CH$_2$— |
| 6.2 | 2 | singlet | —NH$_2$ |
| 6.4 | 1 | singlet | —NH—CH$_2$—CH— |
| 6.6 | 2 | multiplet | —CH= (aromatic ring) |
| 7.0 | 1 | singlet | —CH—CH2—NH— |
| 7.7 | 2 | multiplet | —CH= (aromatic ring) |
| 8.2 | 1 | singlet | —CO—NH—CH— |

TABLE 1-continued

| Chemical shift (ppm) | Number of protons | Multiplicity | Attribution |
|---|---|---|---|
| 8.8 | 1 | singlet | —OH |
| 10.3 | 1 | singlet | —CHO |
| 11.8-12.8 | 2 | singlet (broad) | —COOH (2 x) |

EXAMPLE 2

Two specimens of the product obtained in example 1 are subjected to accelerated stability tests and long-term stability tests, respectively; the tests are carried out according to ICH conditions.

Accelerated: 40±2° C., 75±5% relative humidity
Long-term: 25±2° C., 60±5% relative humidity Analytical methods used for the stability studies tests are described in the calcium levofolinate monograph of the European Pharmacopoeia. The results of the accelerated test are reported in Table 2, while the results of the long-term test are reported in Table 3. In both Tables 2 and 3, "n. t." stands for not tested; 1) indicates that the % area has been calculated on the basis of folinic acid absorption at 280 nm; and 2) indicates that the assay of levofolinic acid has been calculated on the anhydrous and solvent free basis.

TABLE 2

| | | Elapsed time (months) | | |
|---|---|---|---|---|
| Parameter | Specification | 0 | 3 | 6 |
| Appearance | White to pale yellow powder | Conform | Conform | Conform |
| Aspect of a 1.0% w/v solution in Tris buffer solution corrected at pH = 8.1 | | | | |
| Clarity | Clear | < No. 1 | < No. 1 | < No. 1 |
| Absorbance at 420 nm | ≤0.25 | 0.06 | 0.05 | 0.06 |
| Optical rotation of a 1.0% w/v solution in Tris solution corrected at pH = 8.1 | −9.5° to −15.5° | −12.8 | n.t. | n.t. |
| Water content (%) | ≤2.0 | 0.8 | 0.8 | 1.1 |
| Related substances: | | | | |
| PABG (A) (% area) | ≤0.80[1] | <0.10 | <0.10 | 0.13 |
| N$^5$-N$^{10}$-diformyl-THF (B) (% area) | ≤0.80[1] | <0.10 | <0.10 | <0.10 |
| Folic acid (C) (% area) | ≤0.80[1] | <0.10 | <0.10 | <0.10 |
| N$^{10}$—CHO-folic acid (D) (% m/m) | ≤0.80[1] | <0.10 | <0.10 | <0.10 |
| 5-CHO—4H-Pteroic acid (E) (% area) | ≤0.80[1] | 0.36 | 0.37 | 0.33 |
| N$^{10}$—CHO-dihydrofolic acid (F) (% area) | ≤0.80[1] | <0.10 | 0.16 | 0.25 |
| Dihydrofolic acid (G) (% area) | ≤0.80[1] | <0.10 | <0.10 | <0.10 |
| Any individual unknown impurities | ≤0.25[1] | <0.10 | <0.10 | <0.10 |
| Sum of all relates substances (% area) | ≤2.0[1] | 0.57 | 0.63 | 0.84 |
| Content of Dextrofolinic acid (H) | ≤0.50% | <0.10 | n.t. | <0.10 |
| Assay of Levofolinic acid (% m/m)[2] | 98.0-102.0% | 99.7 | 99.9 | 99.0 |

TABLE 3

| | | Elapsed time (months) | | | | | | |
|---|---|---|---|---|---|---|---|---|
| Parameter | Specification | 0 | 3 | 6 | 9 | 12 | 18 | 24 | 36 |
| Appearance | White to pale yellow powder | Conform | Conform | Conform | Conform | Conform | Conform | Conform | Conform |
| Aspect of a 1.0% m/V solution in Tris solution corrected at pH = 8.1 | | | | | | | | | |
| Clarity | Clear | <No. 1 | <No. 1 | <No. 1 | <No. 1 | <No. 1 | <No. 1 | <No. 1 | <No. 1 |
| Absorbance at 420 nm | ≤0.25 | 0.06 | 0.05 | 0.06 | 0.04 | 0.06 | 0.05 | 0.06 | 0.08 |

TABLE 3-continued

| Parameter | Specification | Elapsed time (months) | | | | | | | |
|---|---|---|---|---|---|---|---|---|---|
| | | 0 | 3 | 6 | 9 | 12 | 18 | 24 | 36 |
| Optical rotation of a 1.0% m/V solution in Tris solution corrected at pH = 8.1 | −9.5° to −15.5° | −12.8 | n.t. | n.t. | n.t. | n.t. | −13.1° | n.t. | −14.9° |
| Water content (%) | ≤2.0 | 0.8 | 0.8 | 0.9 | 1.0 | 1.1 | 0.9 | 0.7 | 1.0 |
| Related substances: | | | | | | | | | |
| PABG (A) (% area) | ≤0.80 [1)] | <0.10 | <0.10 | 0.10 | <0.10 | 0.11 | 0.11 | 0.13 | 0.16 |
| $N^5$-$N^{10}$-diformyl-THF (B) (% area) | ≤0.80 [1)] | <0.10 | <0.10 | <0.10 | <0.10 | <0.10 | <0.10 | <0.10 | <0.10 |
| Folic acid (C) (% area) | ≤0.80 [1)] | <0.10 | <0.10 | <0.10 | <0.10 | <0.10 | <0.10 | <0.10 | <0.10 |
| $N^{10}$-CHO-folic acid (D) (% m/m) | ≤0.80 [1)] | <0.10 | <0.10 | <0.10 | <0.10 | <0.10 | <0.10 | <0.10 | <0.10 |
| 5-CHO-4H-Pteroic acid (E) (% area) | ≤0.80 [1)] | 0.36 | 0.31 | 0.34 | 0.35 | 0.34 | 0.36 | 0.31 | 0.33 |
| $N^{10}$-CHO-dihydrofolic acid (F) (% area) | ≤0.80 [1)] | <0.10 | 0.13 | 0.15 | 0.15 | 0.18 | 0.17 | 0.16 | 0.25 |
| Dihydrofolic acid (G) (% area) | ≤0.80 [1)] | <0.10 | <0.10 | <0.10 | <0.10 | <0.10 | <0.10 | <0.10 | <0.10 |
| Any individual unknown impurities | ≤0.25 [1)] | <0.10 | <0.10 | <0.10 | <0.10 | <0.10 | <0.10 | <0.10 | <0.10 |
| Sum of all relates substances (% area) | ≤2.0 [1)] | 0.57 | 0.49 | 0.70 | 0.55 | 0.63 | 0.63 | 0.66 | 0.73 |
| Content of Dextrofolinic acid (H) | ≤0.50% | <0.10 | n.t. | <0.10 | n.t. | n.t. | n.t. | <0.10 | <0.10 |
| Assay of Levofolinic acid (% m/m) [2)] | 98.0-102.0% | 99.7 | 100.6 | 98.8 | 99.4 | 99.4 | 100.2 | 99.4 | 99.6 |

DISCUSSION OF THE RESULTS

The NMR spectrum reported in FIG. 1, and the attributions of signals of the same given in Table 1, confirm that the product obtained following the procedure of example 1 is levofolinic acid.

Figure 2:
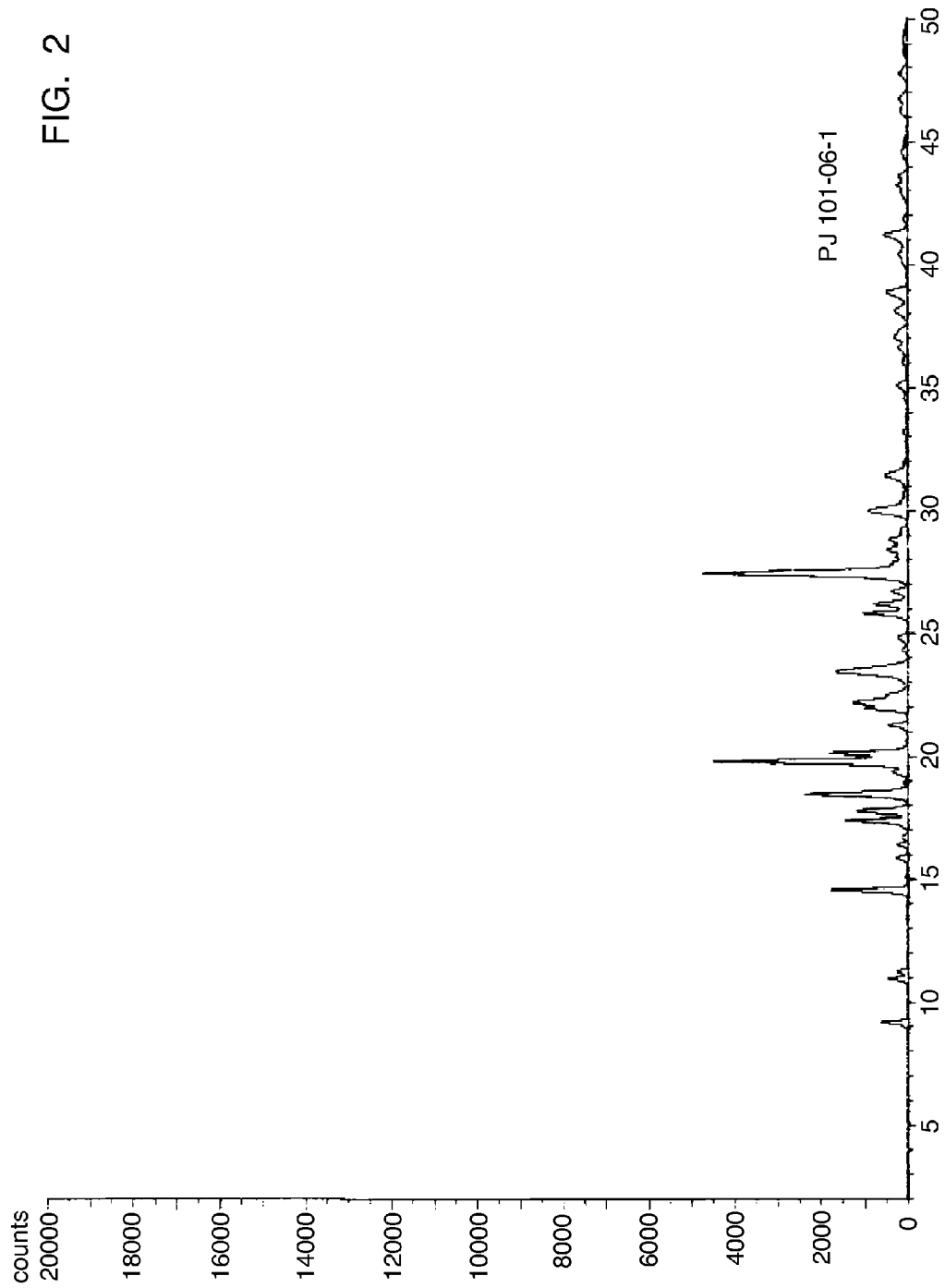
FIG. 2 shows an XRD pattern obtained on powders of levofolinic acid prepared according to the invention.

The XRD diagram reported in FIG. 2 confirms that the product is completely crystalline.

The entries in row "Assay of Levofolinic acid" in Tables 2 and 3 confirm that the obtained product is in fact the desired one, while some "Specifications" values in the same tables confirm that the product is obtained essentially pure and in essentially pure 6S diastereoisomeric form (dextrofolinic acid is only present in traces).

Finally, the stability data of tables 2 and 3 indicate that, surprisingly, the pure crystalline levofolinic acid obtained according to the invention is stable, and may resist unaltered, during a shelf-life of up to three years; in this respect, the product of the invention has better properties than calcium levofolinate of the known art or than levofolinic acid amorphous obtained as described in U.S. Pat. No. 5,134,235.

The invention claimed is:

1. Process for the preparation of stable crystalline (6S)—N(5)-formyl-5,6,7,8-tetrahydrofolic acid in essentially diastereoisomerically pure 6S-form, comprising the steps of:

preparing a first aqueous or hydroalcoholic solution, having a pH value higher than 4.5, of a soluble levofolinate salt;

providing a batch of water, or of a hydroalcoholic mixture containing up to 60% v/v of an alcohol, pre-heated at a temperature between 30 and 60° C.;

forming a second solution, by adding said first solution and a second acid to said batch of water or hydroalcoholic mixture, operating in such a way that the levofolinate salt concentration in the second solution never exceeds 4% w/v, the pH value of the second solution always remains in the range between 3.0 and 4.5, and the temperature of the second solution always remains in the range between 30 and 60° C.;

upon completion of the addition of said first solution to said batch of water or hydroalcoholic mixture, stirring the thus formed second solution while the crystallization of levofolinic acid occurs, maintaining the solution at a temperature between 30 and 60° C., monitoring the pH and continuously adding said second acid to keep the pH stable, until it is observed that the pH value becomes stable with no need of further addition of said second acid, indicating the end of the crystallisation of levofolinic acid;

recovering the crystalline levofolinic acid thus formed.

2. Process according to claim 1 in which, when a hydroalcoholic solution or a hydroalcoholic mixture is used, the alcohol employed is selected among methyl alcool, ethyl alcohol, isopropyl alcohol or mixtures thereof.

3. Process according to claim 1, in which said hydroalcoholic mixture contains between 5 and 10% v/v of alcohol.

4. Process according claim 1, in which said first solution is prepared by dissolving in water or in a hydroalcoholic mixture an alkaline metal levofolinate at a concentration up to 30% w/v.

5. Process according to claim 1, in which said first solution is prepared with an alkaline-earth metal levofolinate, solubilized by heating up to 80° C.

6. Process according to claim 1, in which said first solution is prepared through cation exchange, by suspending an alkaline-earth metal levofolinate in an aqueous or hydroalcoholic solvent in which is dissolved a salt formed by an alkaline metal cation and an anion giving rise to an insoluble salt with said alkaline-earth metal; allowing said insoluble salt to precipitate; and separating and eliminating the precipitated salt from the solution of alkaline metal levofolinate thus obtained.

7. Process according to claim 1, in which the second solution is formed operating so that the levofolinate salt concentration in the second solution is always comprised between 1 and 2.5% w/v.

8. Process according to claim 1, in which, the second acid is selected among HCl, $H_2SO_4$, $H_3PO_4$.

9. Process according to claim 1, wherein recovery of levofolinic acid is performed by centrifugation and/or filtration.

10. Process according to claim 1, further comprising drying of the product by removal of solvent traces under reduced pressure.

11. Stable, crystalline (6S)—N(5)-formyl-5,6,7,8-tetrahydrofolic acid in essentially diastereoisomerically pure 6S-form, characterized in that the corresponding X-ray powder diffraction diagram has the following characteristic 2θ angle values, ±0.2°:
14.4
17.3
17.7
18.3
19.7
20.0
22.1
23.3
27.3.

12. Pharmaceutical preparation comprising stable, crystalline (6S)—N(5)-formyl-5,6,7,8-tetrahydrofolic acid in essentially diastereoisomerically pure 6S-form according to claim 11.

13. Pharmaceutical preparation according to claim 12, wherein said preparation is a vitamin preparation.

14. A method of treating colorectal cancer in a subject in need thereof, comprising administering an effective amount of a compound of claim 11 to said subject.

15. A method of enhancing the influence of a cancer controlling compound in a subject in need thereof, comprising administering a compound of claim 11 to said subject in an amount effective to enhance the influence of the cancer controlling compound 5-fluorouracil.

16. A method of reducing the toxicity of a cancer controlling compound in a subject in need thereof, comprising administering a compound of claim 11 to said subject in an amount effective to reduce the toxicity of the cancer controlling compound methotrexate.

* * * * *